US00PP27824P3

(12) United States Plant Patent
Zaiger et al.

(10) Patent No.: US PP27,824 P3
(45) Date of Patent: Apr. 4, 2017

(54) INTERSPECIFIC TREE NAMED 'KINGS KAT'

(50) Latin Name: **Interspecific *Prunus* species**
Varietal Denomination: Kings Kat

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 73 days.

(21) Appl. No.: 14/756,334

(22) Filed: Aug. 31, 2015

(65) Prior Publication Data

US 2017/0064891 P1 Mar. 2, 2017

(51) Int. Cl.
*A01H 5/08* (2006.01)

(52) U.S. Cl.
USPC ..... Plt./180

(58) Field of Classification Search
USPC ..... Plt./180
See application file for complete search history.

*Primary Examiner* — Anne Grunberg

(57) ABSTRACT

A new and distinct variety of interspecific tree (Interspecific *Prunus* species). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Regular and productive bearer of medium size fruit.
3. Fruit with attractive red skin color.
4. Fruit with very good flavor and eating quality.
5. Fruit with firm, reddish flesh with good storage and shipping ability.

1 Drawing Sheet

Botanical designation: Interspecific *Prunus* species.
Variety denomination: 'Kings Kat'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein, 'Flavorosa' Interspecific (U.S. Plant Pat. No. 10,285), 'Flavor Fusion' Interspecific (U.S. Plant Pat. No. 23,902) and our non-patented proprietary interspecific seedling with the field identification number '63Z241'.

STATEMENT REGARDING FEDERALLY SPONSORED RESEARCH AND DEVELOPMENT

Not applicable.

ORIGIN OF THE VARIETY

The new and distinct interspecific tree consists of *Prunus salicina*×(*Prunus salicina*×*Prunus armeniaca*). It was originated by us in our experimental orchard located near Modesto, Calif. as a first generation cross between 'Flavorosa' Interspecific (U.S. Plant Pat. No. 10,285) and our non-patented interspecific seedling with the field identification number '63Z241'. The non-patented interspecific pollen parent (63Z241) originated as an open pollinated seedling selection from 'Flavorosa' Interspecific (U.S. Plant Pat. No. 10,285). A large number of these first generation seedlings were grown on their own root and under close and careful observation the present seedling exhibited desirable fruit and tree characteristics and was selected in 2005 for additional asexual propagation and commercialization.

ASEXUAL REPRODUCTION OF THE VARIETY

In 2005 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific tree [Plum×(Plum×Apricot)] which has vigorous, upright growth and is a regular and productive bearer of medium size fruit with an attractive reddish skin color. The fruit is further characterized by its firm, reddish flesh, very good flavor and eating quality. In comparison to its seed parent 'Flavorosa' Interspecific (U.S. Plant Pat. No. 10,285) the fruit of the new variety is globose compared to oblate, has lighter red flesh and is approximately 23 days later in maturity. In comparison to its pollen parent (63Z241) interspecific (non-patented) the fruit of the new variety has reddish flesh compared to yellow and is approximately 14 days later in maturity. In comparison to the commercial variety 'Flavor Fusion' Interspecific (U.S. Plant Pat. No. 23,902) the fruit of the new variety is approximately 9 days later in maturity.

DESCRIPTION OF THE PHOTOGRAPH

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 10 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 10 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters the first growing season. Varies slightly with type and fertility of soil, climatic conditions and cultural practices.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 8 consecutive years. No alternate bearing observed.

*Fertility*.—Self-sterile, pollinator required.

*Density*.—Medium dense, usually pruned to vase shape to increase air movement and sunlight to enhance fruit color and health of fruit spurs.

*Hardiness*.—Hardy in all stone fruit growing areas of California. Tree grown in USDA Hardiness Zone 9. Winter chilling requirement approximately 700 hours at or below 45° F.

Trunk:

*Size*.—Large, average circumference 66.0 cm at 23.0 cm above ground on a 10 year old tree.

*Stocky*.—Medium stocky.

*Texture*.—Medium shaggy, roughness increases with age.

*Color*.—Varies from 7.5YR 2/2 to 10YR 2/2.

Branches:

*Size*.—Medium. Average circumference 11.9 cm at 1.2 meters above ground. Crotch angle approximately 35°, increases with heavy crop load.

*Lenticels*.—Average number 54 in a 25.8 square cm area. Average length 4.5 mm. Average width 2.2 mm. Color varies from 7.5YR 2/2 to 10YR 2/2.

*Color*.—New growth varies from 5GY 5/6 to 5GY 5/8. Mature growth varies from 7.5YR 2/2 to 10YR 2/2, varies with age of growth.

Leaves:

*Size*.—Medium to large. Average length 126.9 mm. Average width 62.0 mm.

*Form*.—Oblanceolate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Medium. Average length 16.2 mm. Average width 1.8 mm. Longitudinally grooved. Surface — glabrous. Color varies from 2.5GY 5/6 to 5GY 5/6.

*Glands*.—Type — globose. Number varies from 1 to 3, average number 2. Size — medium. Average length 1.2 mm. Average diameter 0.8 mm. Located primarily on the base of the leaf blade and the upper portion of the petiole. Color varies from 5GY 6/6 to 2.5GY 6/8.

*Stipules*.—Average number 2. Average length 5.0 mm. Edges — pectinate. Color varies from 2.5GY 6/8 to 2.5GY 5/6.

*Color*.—Upper surface varies from 5GY 3/4 to 7.5GY 3/4. Lower surface varies from 7.5GY 4/4 to 5GY 4/4. Midvein color varies from 2.5GY 5/4 to 5GY 5/4.

Flower buds:

*Size*.—Medium to large. Average length 9.9 mm. Average diameter 6.5 mm.

*Hardiness*.—Hardy with respect to California winters.

*Density*.—Medium.

*Form*.—Conical, becoming elongated just before opening.

*Pedicel*.—Average length 7.9 mm. Average width 0.7 mm. Color varies from 2.5GY 8/6 to 5GY 6/10. Surface — glabrous.

*Color*.—N 9.5/(white).

*Number of buds per spur*.—Varies from 5 to 9, average number 7. Varies with age of spur.

Flowers:

*Blooming period*.—Date of First Bloom Feb. 8, 2015. Date of Last Bloom Feb. 18, 2015, varies slightly with climatic conditions.

*Size*.—Medium to large. Average height 11.1 mm. Average diameter 22.5 mm.

*Petals*.—Normally 5, alternately arranged to sepals. Petal apex rounded. Petal base truncated. Size — medium to large. Average length 12.0 mm. Average width 8.7 mm. Form — globose. Arrangement — free. Margin — sinuate. Both upper and lower surfaces glabrous. Color N 9.5/(white).

*Sepals*.—Normally 5, alternately arranged to petals. Size — medium. Average length 3.9 mm. Average width 3.1 mm. Shape — ovate to triangular. Apex — rounded to triangular. Margin — entire. Both upper and lower surfaces glabrous. Color — upper surface varies from 5GY 6/10 to 5GY 5/10. Lower surface varies from 5GY 5/8 to 5GY 5/10.

*Stamens*.—Average number per flower 36. On average the stamens are even with the height of the petals. Average filament length 7.6 mm. Filament color N 9.5/(white). Anther color 2.5YR 5/10 to 5Y 8.5/8.

*Pollen*.—Self-sterile, pollinator required. Color varies from 2.5Y 7/12 to 5Y 7/12.

*Pistil*.—Number — normally 1. Average length 8.5 mm. Position of stigma an average of 0.5 mm below anthers. Surface — glabrous. Color varies from 10Y 8/6 to 2.5GY 8/6.

*Fragrance*.—Moderate.

*Color*.—N 9.5/(white).

*Pedicel*.—Average length 8.5 mm. Average width 0.7 mm. Color varies from 5GY 7/10 to 5GY 5/10. Surface — glabrous.

*Number flowers per flower bud*.—Average 2, varies from 1 to 3.

Fruit:

*Maturity when described*.—Firm ripe, and ready for consumption.

*Date of first picking*.—Jun. 16, 2015.

*Date of last picking*.—Jun. 26, 2015, varies slightly with climatic conditions.

*Size*.—Medium. Average diameter axially 57.5 mm. Average transversely in suture plane 65.5 mm. Average weight 147.7 grams, varies slightly with fertility of the soil, amount of thinning and climatic conditions.

*Form*.—Globose.

*Suture*.—Nearly smooth.

*Ventral surface*.—Nearly smooth.

*Apex*.—Rounded to slight tip.

*Base*.—Retuse.

*Stem cavity*.—Rounded to slightly elongated in suture plane. Average depth 5.7 mm. Average diameter 3.5 mm.

Stem:

*Size*.—Large. Average length 17.3 mm. Average diameter 2.3 mm.

*Color*.—Varies from 10Y 6/8 to 2.5GY 5/6.

Flesh:

*Ripens*.—Slightly early at apex.

*Texture*.—Firm, meaty.

*Fibers*.—Few, small, tender.

*Firmness*.—Good, comparable to other commercial varieties.

*Aroma*.—Slight.

*Amydgalin*.—Undetected.

*Eating quality*.—Very good.

*Flavor*.—Sub-acid.

*Juice*.—Moderate amount, enhances flavor.

*Acidity*.—Not available.

*Brix*.—Average Brix 14.2°, varies slightly with amount of fruit per tree and climatic conditions.

*Color*.—Varies from 5R 3/10 to 10YR 8/2.

*Pit cavity*.—Average length 27.7 mm. Average. width 19.5 mm. Average depth 8.3 mm. Color varies from 10R 4/10 to 2.5YR 4/8.

Skin:

*Thickness*.—Medium.

*Surface*.—Smooth.

*Bloom*.—Moderate.

*Tendency to crack*.—None.

*Color*.—Ground color varies from 5YR 5/8 to 7.5Y 5/8. Overspread with 10R 2/6 to 10R 2/4.

*Tenacity*.—Tenacious to the flesh.

*Astringency*.—Undetected.

Stone:

*Type*.—Clingstone. Adherence to flesh present, medium.

*Size*.—Medium. Average length 24.5 mm. Average width 20.5 mm. Average thickness 8.8 mm.

*Form*.—Elliptical.

*Base*.—Flat.

*Apex*.—Rounded to slight tip. Average length 1.3 mm.

*Surface*.—Slightly pitted throughout. One shallow groove on each side of suture extending from base to apex.

*Sides*.—Unequal, one side extending further from suture plane.

*Ridges*.—Relatively smooth, extending from base to apex.

*Tendency to split*.—None.

*Color*.—Varies from 10YR 6/6 to 7.5YR 6/6 when dry.

Kernel:

*Size*.—Small. Average length 11.3 mm. Average width 7.9 mm. Average depth 3.5 mm.

*Form*.—Elliptical.

*Viability*.—Viable, complete embryo development.

*Skin color*.—Varies from 7.5Y 9/4 to 5Y 9/4.

Use: Dessert.

*Market*.—Local and long distance.

Keeping quality: Good, held firm in cold storage 3 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

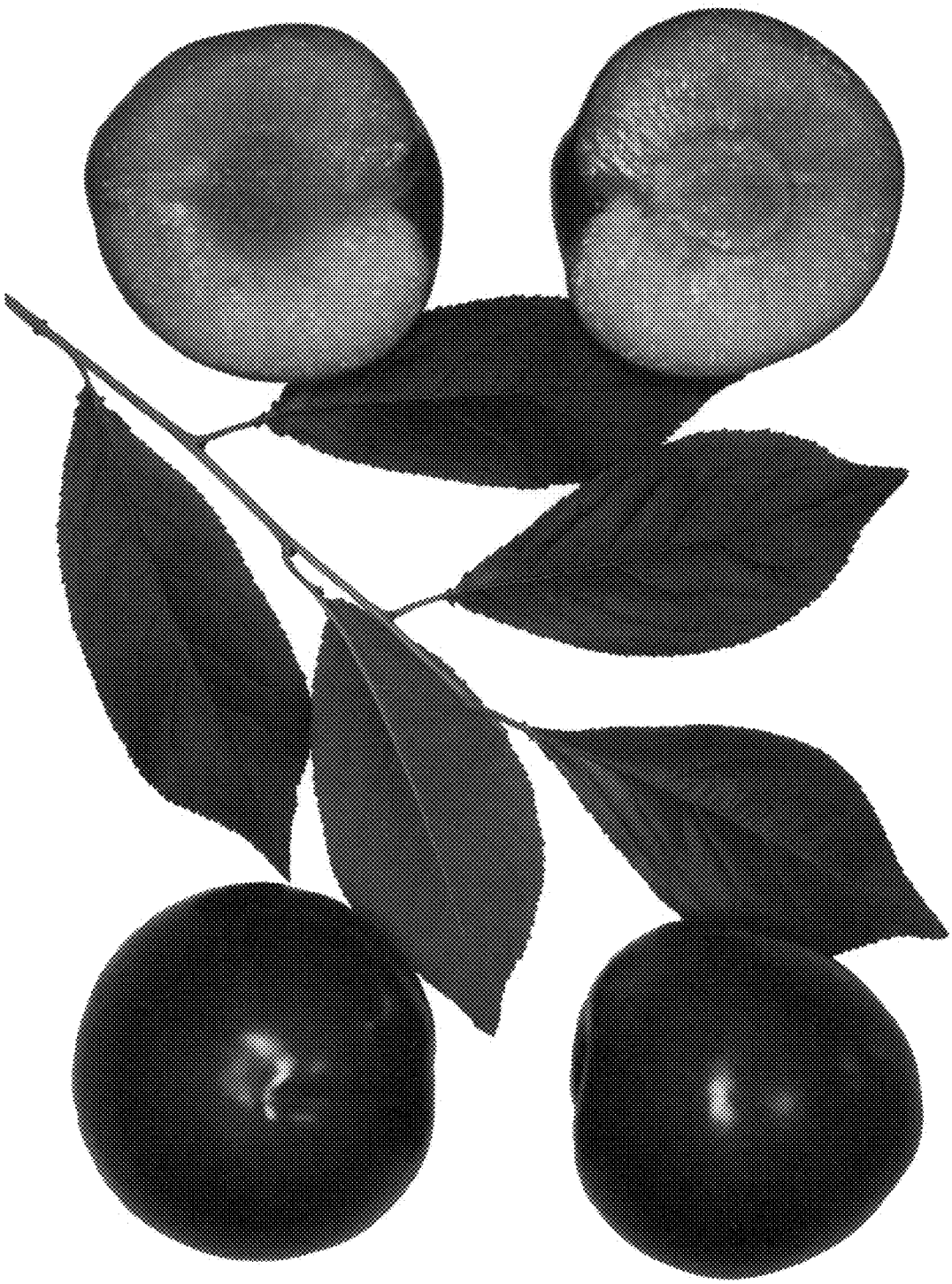

* * * * *